(12) United States Patent
Schafer

(10) Patent No.: US 7,229,442 B2
(45) Date of Patent: Jun. 12, 2007

(54) CERVICAL VERTEBRA PLATE

(75) Inventor: Bernd Schafer, Oberägeri (CH)

(73) Assignee: DePuy Spine Sàrl, Le Locle (CH)

( * ) Notice: Subject to any disclaimer, the term of this patent is extended or adjusted under 35 U.S.C. 154(b) by 80 days.

(21) Appl. No.: 10/527,339

(22) PCT Filed: Sep. 11, 2003

(86) PCT No.: PCT/EP03/10104

§ 371 (c)(1),
(2), (4) Date: Mar. 10, 2005

(87) PCT Pub. No.: WO2004/026159

PCT Pub. Date: Apr. 1, 2004

(65) Prior Publication Data

US 2006/0142766 A1    Jun. 29, 2006

(30) Foreign Application Priority Data

Sep. 17, 2002   (DE) .............................. 102 43 791

(51) Int. Cl.
*A61B 17/56* (2006.01)
(52) U.S. Cl. .......................................... 606/61; 606/69
(58) Field of Classification Search .................. 606/61, 606/69–71; 411/161–163, 173–175, 187, 411/214, 307, 451.4
See application file for complete search history.

(56) References Cited

U.S. PATENT DOCUMENTS

| 388,000 | A | * | 8/1888 | Rider ........................... 411/399 |
|---|---|---|---|---|
| 1,151,861 | A | * | 8/1915 | Brumback ................... 411/399 |
| 5,199,839 | A | * | 4/1993 | DeHaitre .................. 411/387.3 |
| 5,275,601 | A | * | 1/1994 | Gogolewski et al. .......... 606/72 |
| 5,564,873 | A | * | 10/1996 | Ladouceur et al. .......... 411/180 |
| 5,607,428 | A | * | 3/1997 | Lin .............................. 606/69 |
| 5,772,376 | A | * | 6/1998 | Konig ........................ 411/399 |
| 6,306,136 | B1 | | 10/2001 | Baccelli |
| 6,394,725 | B1 | * | 5/2002 | Dicke ......................... 411/399 |
| 6,613,053 | B1 | * | 9/2003 | Collins et al. ................ 606/69 |
| 7,052,499 | B2 | * | 5/2006 | Steger et al. ................. 606/69 |
| 2001/0035075 | A1 | | 11/2001 | Amis | |

FOREIGN PATENT DOCUMENTS

| DE | 44 09 833 | 10/1995 |
|---|---|---|
| DE | 199 50 270 | 5/2001 |

\* cited by examiner

*Primary Examiner*—Eduardo C. Robert
*Assistant Examiner*—Tara George
(74) *Attorney, Agent, or Firm*—Paul Vincent

(57) ABSTRACT

The invention relates to a cervical vertebra plate (10) for osteosynthesis, having two receiving openings for the screw heads (18) of bone screws (16) in order to secure the cervical vertebra plate to two cervical vertebrae. The receiving openings have grooves (22) in the distal region on the periphery thereof and the depth of the grooves increases from a proximal to a distal end. The invention also relates to a bone screw (18) comprising a screw head (16) and a screw shank. The screw head comprises grooves (34) on the outer periphery thereof and the depth of the grooves varies along the length thereof.

12 Claims, 2 Drawing Sheets

CERVICAL VERTEBRA PLATE

This application is the national stage of PCT/EP2003/010104 filed on Sep. 11, 2003 and also claims Paris Convention priority of DE 102 43 791.2 filed on Sep. 17, 2002.

BACKGROUND OF THE INVENTION

The invention concerns a cervical vertebra plate for osteosynthesis, having at least two receiving openings for the screw heads of bone screws to secure the cervical vertebra plate to two cervical vertebrae, wherein the receiving openings have a fluting, in particular a longitudinal fluting, in the distal region about the periphery thereof. The invention also concerns a bone screw, in particular, for a cervical vertebra plate of this type, comprising a screw head and a threaded screw shank, wherein the outer periphery of the screw head has a fluting, in particular, a longitudinal fluting.

Bone plates are known per se, e.g. from DE 199 50 270 A1. Bone plates of this type are e.g. secured to vertebrae to orient and stabilize them. Towards this end, the individual bone plates are connected via rods, wherein the rods are mounted, in particular clamped, to the bone plates.

Bone screws are used to secure the bone plates to vertebrae. The screws penetrate through the bone plates and are screwed into the vertebra. The bone plate is usually held via the screw head.

U.S. Pat. No. 5,275,601 also discloses a bone screw which is supported with its fluted conical screw head in a receiving opening of a plate. The plate is secured to the bone via these screws.

It is the underlying purpose of both of these bone plates to optimally adopt the forces acting on the bone such that they are either transferred to a neighboring bone or bone part or to correction or fixation rods. Towards this end, the screw head must in any case be optimally supported in the receiving opening of the bone plate to prevent play between the screw head and receiving opening. Securing to prevent inadvertent unscrewing is effected by the fluting provided on the inner periphery of the receiving opening and/or the outer periphery of the screw head.

It is the underlying purpose of the present invention to introduce a system which provides a safer, tight connection, i.e. optimum support of the outer peripheral surface of the screw head on the inner peripheral surface of the receiving opening of the bone plate.

This object is achieved in accordance with the invention with a cervical vertebra plate of the above-mentioned type in that the depth of the fluting increases from a proximal to a distal end.

SUMMARY OF THE INVENTION

The inventive cervical vertebra plate also has a fluting on the inner periphery of the receiving opening. However, the depth of the fluting is not constant but increases in the distal direction. The fluting may extend over the entire length of the receiving opening. This is, however, not absolutely necessary. In the inventive cervical vertebra plate, the screw head is advantageously positively supported on the proximal side of the receiving opening over a large area of the inner peripheral surface. This region of positive support gradually decreases in a distal direction. The tight support of the screw head in the proximal area ensures that the bone plate is optimally and positively held in the direct vicinity of the bone by the bone screw. The forces exerted on the bone are thereby introduced into the bone plate directly at the bone surface via the bone screw, i.e. via the screw head. This is advantageous in that no bending moments act on the screw and the screw may therefore be smaller in size as is particularly important in the region of cervical vertebrae, since these vertebrae are small and prevent use of large implants.

To improve the seat of the bone screw, in particular its positive locking, the receiving openings in the cervical vertebra plate widen in a distal direction. The receiving openings are advantageously conical or dome-shaped. The screw head may thereby be sunk in the cervical vertebra plate to positively abut the inner peripheral surface of the receiving opening when the screw is tightened.

The fluting is preferably wedge-shaped. The conical flanks which face the inner space of the receiving opening, can thereby advantageously dig into the outer surface of the screw head or hook to the screw head, to provide protection against unscrewing.

In a preferred embodiment, the cervical vertebra plate has four receiving openings which are located in the corner regions of the cervical vertebra plate. In this manner, two neighboring cervical vertebrae can be secured to the cervical vertebra plate using two bone screws each. This permits transfer of tensile and compression forces and also of torsion and shearing forces.

In a further development, a further receiving opening is provided in the center of the cervical vertebra plate. A bone screw may be screwed into this further central receiving opening, in particular if the vertebrae are incomplete or difficult to access, to provide a further possibility of connecting this vertebra to the cervical vertebra plate.

The above-mentioned object is also achieved in accordance with the invention with a bone screw of the above-mentioned type in that the fluting has a varying depth along its length.

In this manner, the supporting region on the outer peripheral surface of the screw head, with which the screw head positively abuts the inner peripheral surface of the receiving opening is enlarged as is the case for the inner peripheral surface of the receiving opening of the cervical vertebra plate. Optimum, secure force transfer between the vertebra and the cervical vertebra plate is thereby also facilitated by the bone screw.

In a further development, the screw head is substantially a truncated cone and the depth of the fluting increases from the proximal to the distal end. This is advantageous in that the supporting area, i.e. The area of the screw head which positively abuts the inner peripheral surface of the receiving opening is located in the proximal area. In this fashion, the forces are introduced from the vertebra into the cervical vertebra plate directly at the vertebra surface, as was mentioned above. The vertebra is supported without substantial bending forces acting on the bone screw, which allows the bone screw to be relatively small in size.

In another embodiment, the screw head is substantially spherical and the depth of the fluting increases from the poles in the direction of the equator, in each case. The individual sections of the fluting substantially have the shape of a spherical segment such that the screw head has large supporting surfaces in the distal area and also in the proximal area.

The longitudinal fluting is preferably formed by wedge-shaped, substantially longitudinal grooves with the individual grooves being separated from each other. As viewed in the peripheral direction, there are smooth sections between the fluting. These areas without grooves also provide positive abutment of the screw head on the inner peripheral surface of the receiving opening of the cervical vertebra plate, to facilitate screwing of the screw. Screwing of the screw is not impaired by the fluting on the inner peripheral surface of the receiving opening or on the outer peripheral surface of the screw head, and the supporting area is also enlarged.

The length of the area without grooves, viewed in the peripheral direction, preferably corresponds to 0.3 and 2.0, in particular between 0.5 and 1.0 times the length of the grooves themselves. In case of smaller or narrower areas without grooves, the screw head may bend more easily during screwing or directly before screwing is terminated to hook with the grooves or with the fluting in the receiving opening of the cervical vertebra plate and thereby be secured against unscrewing. If there are large regions without grooves, the screw head has relatively large abutment surfaces to assure optimum force transmission.

Further advantages, features and details of the invention can be extracted from the following detailed description of preferred embodiments with reference to the drawings. The features shown in the drawing, and mentioned in the description and the claims may be essential to the invention either individually or in arbitrary combination.

BRIEF DESCRIPTION OF THE DRAWING

Figure 1:
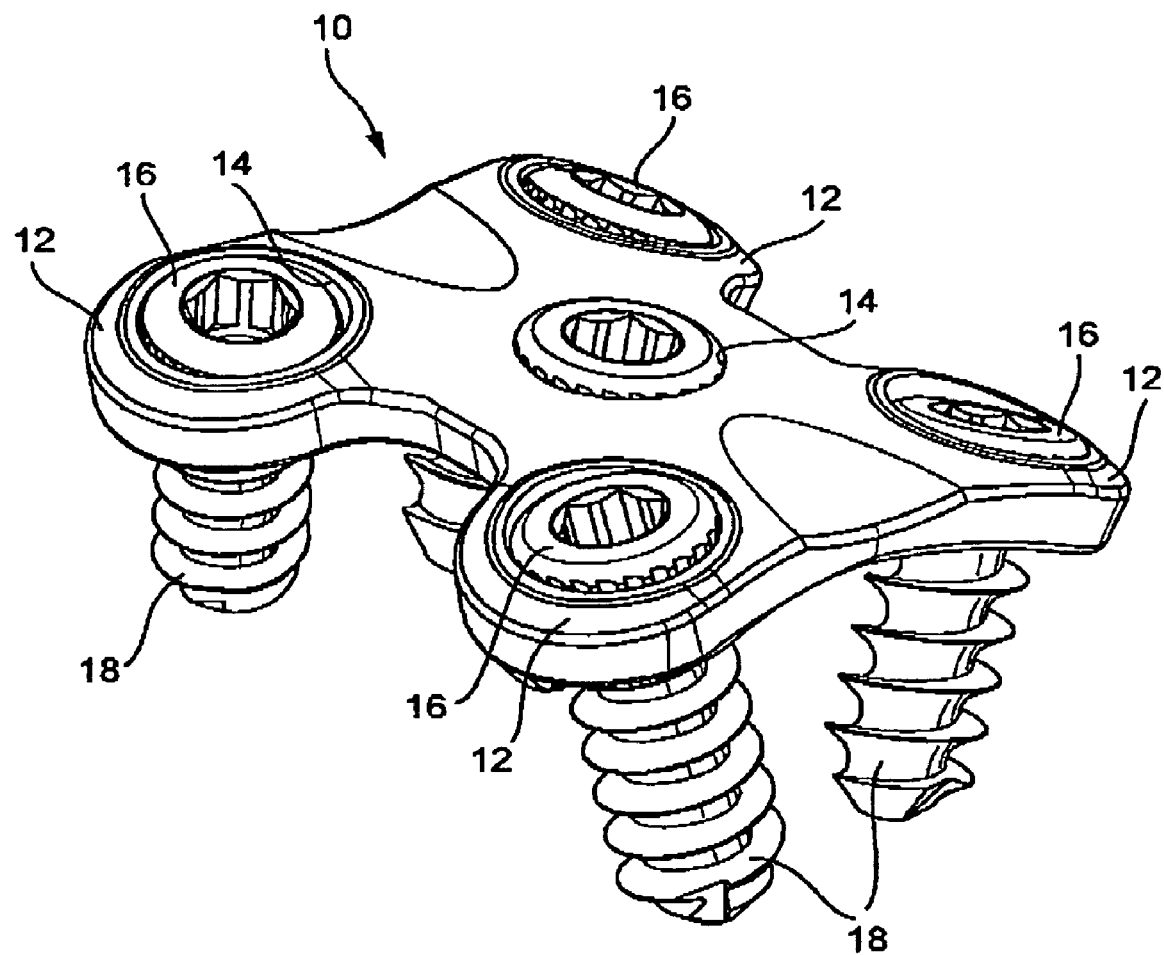
FIG. 1 shows a perspective view of a cervical vertebra plate with inserted bone screws.

FIG. 1 shows a cervical vertebra plate which is designated in total by 10 and has a substantially H-shape. The corner regions 12 have receiving openings 14 (FIG. 2) which receive screw heads 16 (see also FIGS. 3 and 4) of bone screws 18. The cervical vertebra plate 10 has a further receiving opening in its center which bears a further bone screw 18.

The cervical vertebra plate 10 connects two cervical vertebrae, wherein two bone screws 18 are screwed into one cervical vertebra and the two other bone screws 18 are screwed into the other cervical vertebra. The central bone screw is used if a cervical vertebra is incomplete or if one of the bone screws 18 disposed in the corner areas 12 cannot be screwed into a cervical vertebra.

Figure 2:
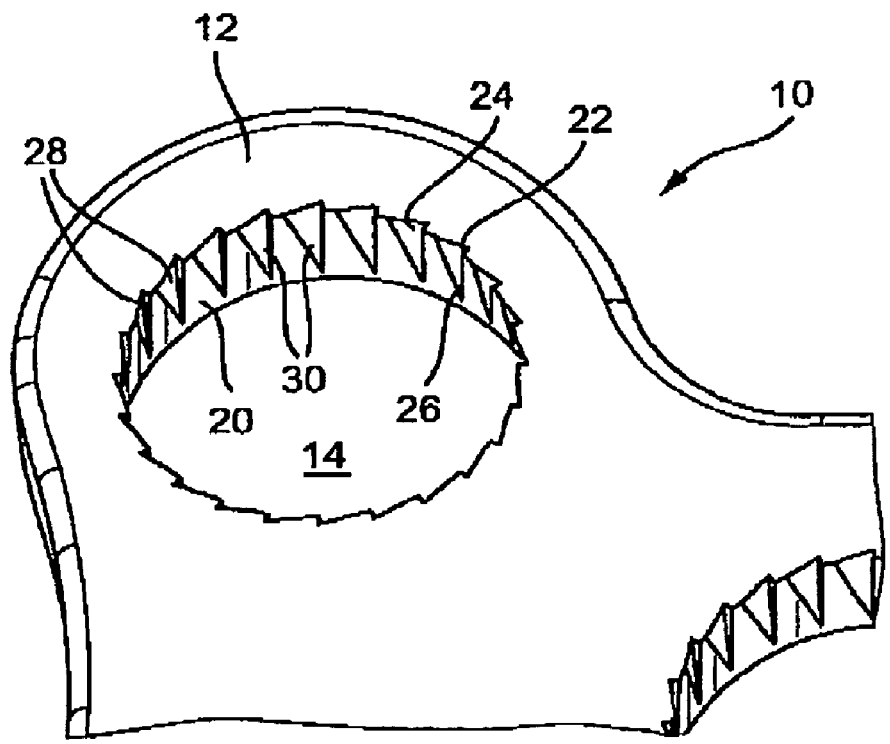
FIG. 2 shows an enlarged illustration of a corner area of the cervical vertebra plate showing a receiving opening.

The receiving opening 14 has an inner peripheral surface 20 which is provided with fluting 22, in particular, a longitudinal fluting (FIG. 2). The fluting 22 extends from the distal end 24 of the receiving opening 20 but not entirely to the proximal end 26, rather merely through approximately 80% of the thickness of the cervical vertebra plate 10. The depth of the fluting 22 changes along the height of the receiving opening 14 and increases from the proximal end 26 towards the distal end 24, thereby producing a fluting 22 with approximately wedge-shaped grooves 28. Neighboring grooves 28 border areas 30 without grooves. These areas 30 without grooves provide positive abutment of the screw head 16 and force transfer between screw head 16 and cervical vertebra plate 10.

FIG. 2 also shows that the width of the areas 30 without grooves increases in the proximal direction such that the screw head 16 positively abuts over the entire periphery in the region of the proximal end 26.

Figure 3:
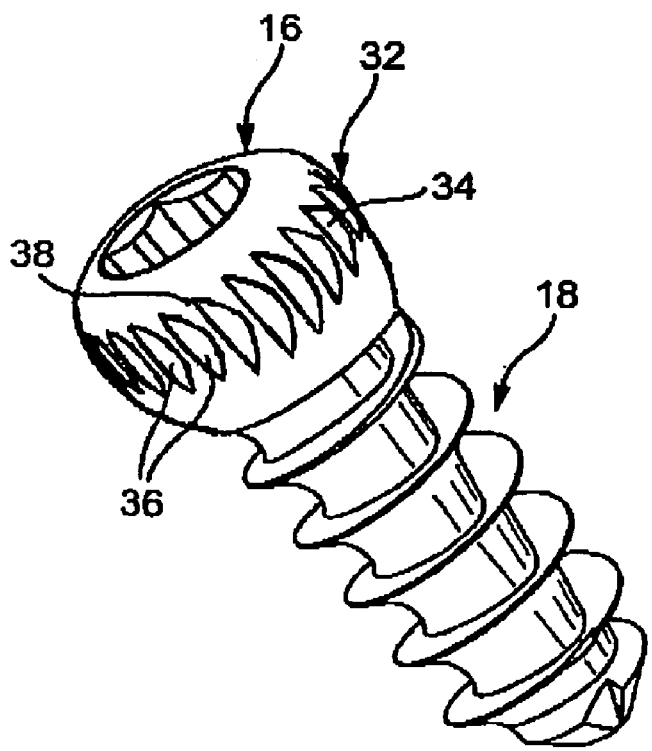
FIG. 3 shows a perspective view of a bone screw.

Fig 3 shows an embodiment of a bone screw 18 having a spherical screw head 16. The outer periphery 32 of the screw head 16 is also provided with a fluting 34 which is formed by the spherical segment-shaped grooves 36. The depth of each groove 36 thereby increases from the proximal end of the screw head 16 towards the distal end and decreases again from the equator (maximum diameter of the screw head 16). An area 38 without grooves is also provided between the individual grooves 36, whose width increases from the equator in the direction towards the proximal and distal ends.

The fluting 22 of the cervical vertebra plate 10 and the fluting 34 of the bone screw 18 are designed to permit screwing in of the bone screw 18 but exert a blocking effect in the opposite direction such that the bone screw 18 does not loosen in the receiving opening 14 due to slight unscrewing.

I claim:

1. A system for osteosynthesis, the system comprising:
a cervical vertebra plate having at least two receiving openings for screw heads of bone screws to secure said cervical vertebra plate to two cervical vertebrae, wherein said receiving openings have a first fluting, disposed about a periphery of a distal area, wherein a depth of said first fluting increases from a proximal towards a distal side of said openings; and
a bone screw having a screw head and a threaded screw shank, wherein a outer periphery of said screw head has a second fluting having a varying depth along a length thereof, wherein said screw head is substantially spherical and said second fluting has a depth which increases from each pole towards an equator of said screw head.

2. The system of claim 1, wherein said first and said second fluting extend in a longitudinal direction.

3. The system of claim 1, wherein said receiving openings widen in a distal direction.

4. The system of claim 3, wherein said openings widen in a conical or dome-shaped fashion.

5. The system of claim 1, wherein said first and said second flutings are wedge-shaped.

6. The system of claim 1, wherein said plate has four receiving openings which are located in corner areas of said plate.

7. The system of claim 6, wherein said plate has a further receiving opening disposed in a center of said plate.

8. The system of claim 1, wherein said first fluting is formed by wedge-shaped grooves which extend in a substantially longitudinal direction, individual grooves having a mutual separation bordering groove-free regions.

9. The system of claim 1, wherein said second fluting is formed by wedge-shaped grooves which extend substantially in a longitudinal direction, with individual grooves being separated from each other.

10. The system of claim 1, wherein, viewed in a peripheral direction, areas without grooves are disposed between groves of said first and said second fluting.

11. The system of claim 1, wherein, viewed in a peripheral direction, a length of said area without grooves is between 0.3 and 2.0 or between 0.5 to 1.0 times a length of said groove.

12. The system of claim 1, wherein said first and said second fluting are structured and dimensioned to cooperate with another to allow said bone screw to be screwed into the cervical vertebra and, following completion of a screwing procedure, to block rotation which would loosen said bone screw.

* * * * *